United States Patent [19]
Vesely

[11] Patent Number: 5,817,022
[45] Date of Patent: Oct. 6, 1998

[54] SYSTEM FOR DISPLAYING A 2-D ULTRASOUND IMAGE WITHIN A 3-D VIEWING ENVIRONMENT

[75] Inventor: Ivan Vesely, Cleveland Heights, Ohio

[73] Assignee: Sonometrics Corporation, London, Canada

[21] Appl. No.: 815,386

[22] Filed: Mar. 11, 1997

Related U.S. Application Data

[63] Continuation-in-part of PCT/CA96/00194 Mar. 24, 1996 which is a continuation-in-part of Ser. No. 411,959, Mar. 28, 1995, Pat. No. 5,515,853.

[51] Int. Cl.$^6$ .......................................................... A61B 8/00
[52] U.S. Cl. ............................................ 600/443; 128/916
[58] Field of Search ..................................... 600/441, 443, 600/444, 445, 446, 447, 461, 462, 459; 128/916; 73/621, 624, 626

[56] References Cited

U.S. PATENT DOCUMENTS

| | | |
|---|---|---|
| 4,173,228 | 11/1979 | VanSteenwyk et al. . |
| 4,304,239 | 12/1981 | Perlin . |
| 4,431,005 | 2/1984 | McCormick . |
| 4,444,195 | 4/1984 | Gold . |
| 4,499,493 | 2/1985 | Nishimura . |
| 4,522,212 | 6/1985 | Gelinas et al. . |
| 4,573,473 | 3/1986 | Hess . |
| 4,613,866 | 9/1986 | Blood . |
| 4,628,937 | 12/1986 | Hess et al. . |
| 4,649,924 | 3/1987 | Taccardi . |
| 4,697,595 | 10/1987 | Breyer et al. . |
| 4,699,147 | 10/1987 | Chilson et al. . |
| 4,777,955 | 10/1988 | Brayton et al. . |
| 4,812,976 | 3/1989 | Lundy . |
| 4,821,731 | 4/1989 | Martinelli et al. . |
| 4,899,750 | 2/1990 | Ekwall . |
| 4,922,912 | 5/1990 | Watanabe . |
| 4,932,414 | 6/1990 | Coleman et al. ................... 128/600.09 |
| 4,940,064 | 7/1990 | Desai . |

(List continued on next page.)

FOREIGN PATENT DOCUMENTS

| | | |
|---|---|---|
| 0 152 905 | 8/1985 | European Pat. Off. . |
| 92301264.5 | 2/1992 | European Pat. Off. . |
| 0 591 899 | 10/1993 | European Pat. Off. . |
| 3904914 | 8/1990 | Germany . |
| 41 19 150 | 12/1992 | Germany . |
| US94/08352 | 7/1994 | WIPO . |
| US94/11298 | 10/1994 | WIPO . |
| US95/01103 | 1/1995 | WIPO . |
| PCT/CA96/00194 | 3/1996 | WIPO . |

OTHER PUBLICATIONS

Davis J.W., Improved Arrival Time Detection for Cardiac Pulse Transit Sonomicrometry, *Computers in Cardiology 1996*, pp. 145–459, 1996.

Morse, Wayne, Medical Electronics, *IEEE Spectrum*, pp. 99–102, Jan. 1997.

Josephson et al., Comparison of Endocardial Catheter Mapping with Intraoperative Mapping of Ventricular Tachycardia, *Circulation*, vol. 61, No. 2, pp. 395–404, 1980.

Josephson et al., Ventricular Tachycardia during Endocardial Pacing . II. Role of Pace–Mapping to Localize Origin of Ventricular Tachycardia, *The American Journal of Cardiology*, vol. 50, pp. 11–22, Jul. 1982.

(List continued on next page.)

*Primary Examiner*—George Manuel
*Attorney, Agent, or Firm*—Benesch, Friedlander, Coplan & Aronoff LLP

[57] ABSTRACT

A system for displaying a 2-D ultrasound image in a 3-D viewing environment. Within the same 3-D viewing environment, various surgical instruments can be tracked and displayed, thus correlating 3-D virtual surgery with ultrasound imaging for verification. A detachable housing (220) containing position transducers (222) is attached to a conventional 2-D ultrasound imaging head (200) to provide position data of an imaging plane generated by an image transducer (204).

13 Claims, 6 Drawing Sheets

U.S. PATENT DOCUMENTS

| | | |
|---|---|---|
| 4,945,305 | 7/1990 | Blood . |
| 5,000,190 | 3/1991 | Petre . |
| 5,012,814 | 5/1991 | Mills et al. . |
| 5,016,173 | 5/1991 | Kenet et al. ............................. 382/128 |
| 5,025,786 | 6/1991 | Siegel . |
| 5,041,973 | 8/1991 | Lebron et al. . |
| 5,042,486 | 8/1991 | Pfeiler et al. ........................... 128/653 |
| 5,054,492 | 10/1991 | Scribner et al. . |
| 5,054,496 | 10/1991 | Wen et al. . |
| 5,056,517 | 10/1991 | Fenici . |
| 5,081,993 | 1/1992 | Kitney et al. . |
| 5,104,393 | 4/1992 | Isner et al. . |
| 5,154,501 | 10/1992 | Svenson et al. . |
| 5,156,151 | 10/1992 | Imran . |
| 5,158,092 | 10/1992 | Glace . |
| 5,161,536 | 11/1992 | Vilkomerson et al. . |
| 5,172,699 | 12/1992 | Svenson et al. . |
| 5,220,924 | 6/1993 | Frazin . |
| 5,222,501 | 6/1993 | Ideker et al. . |
| 5,246,016 | 9/1993 | Lieber et al. . |
| 5,295,484 | 3/1994 | Marcus et al. . |
| 5,297,549 | 3/1994 | Beatty et al. . |
| 5,341,807 | 8/1994 | Nardella . |
| 5,357,956 | 10/1994 | Nardella . |
| 5,379,769 | 1/1995 | Ito et al. ................................. 600/441 |
| 5,391,199 | 2/1995 | Ben-Haim . |
| 5,443,489 | 8/1995 | Ben-Haim . |
| 5,480,422 | 1/1996 | Ben-Haim . |
| 5,485,842 | 1/1996 | Quistgaard ............................. 128/916 |
| 5,515,853 | 5/1996 | Smith et al. . |
| 5,517,990 | 5/1996 | Kalfas et al. . |
| 5,546,951 | 8/1996 | Ben-Haim . |
| 5,582,173 | 12/1996 | Li ........................................... 600/443 |

OTHER PUBLICATIONS

Witkowski et al., An Automated Simultaneous Transmural Cardiac Mapping System, *American Journal of Physiology*, vol. 247, pp. H661–H668, 1984.

Fann et al., Endocardial Activation Mapping and Endocardial Pace–Mapping Using a Balloon Apparatus, *American Journal of Cardiology*, vol. 55, pp. 1076–1083, Apr. 1, 1985.

Tweddell et al., Potential Mapping in Septal Tachycardia: Evaluation of a New Intraoperative Mapping Technique; *Circulation*, vol. 80 (Supplement I), No. 3, pp. I–97 –I–108, Sep. 1989.

Hauer et al., Endocardial Catheter Mapping: Wire Skeleton Techniques for Representation of Computed Arrhythmogenic Sites Compared with Intraoperative Mapping, *Circulation*, vol. 74. No. 6. pp. 1346–1354, Dec. 1986.

Pogwizd et al., Reentrant and Nonreentrant Mechanisms Contribute to Arrhythmogenesis During Early Myocardial Ischemia: Results Using Three–Dimensional Mapping, *Circulation Research*, vol. 61, No. 3, pp. 352–371, Sep. 1987.

Huang et al., Radiofrequency Catheter Ablation of the Left and Right Ventricles: Anatomic and Electrophysiologic Observations, *Pace*, vol. II, pp. 449–459, Apr. 1988.

Jackman et al., New Catheter Techniques for Recording Left Free–Wall Accessory Atrioventricular Pathway Activation, *Circulation*, vol. 78, No. 3, pp. 598–611, Sep. 1988.

Shenasa et al., Cardia Mapping, Part I: Wolff–Parkinson–White Syndrome, *Pace*, vol. 13, pp. 223–230, Feb. 1990.

Scheinman et al., Current Role of Catheter Ablative Procedures in Patients with Cardiac Arrhythmias, *Circulation*, vol. 83, No. 6, pp. 2146–2153, Jun. 1991.

Buckles et al., Computer–Enhanced Mapping of Activation Sequences in the Surgical Treatment of Supraventricular Arrhythmias, *Pace*, vol. 13, Pt. 1, pp. 1401–1407, Nov. 1990.

Tanigawa et al., Prolonged and Fractionated Right Atrial Electrograms During Sinus Rhythm in Patients with Paroxysmal Atrial Fibrillation and Sick Sinus Node Syndrome, *Journal of American College of Cardiologists*, vol. 17, No. 2, pp. 403–408, Feb. 1991.

Kaltenbrunner et al., Epicardial and Endocardial Mapping of Ventricular Tachycardia in Patients with Myocardial Infarction, *Circulation*, vol. 83, No. 3, pp. 1058–1071, Sep. 1991.

Masse et al., A Three–Dimensional Display for Cardiac Activation Mapping, *Pace*, vol. 14, Pt. 1, pp. 538–545, Apr. 1991.

Desai et al., Orthogonal Electrode Catheter Array for Mapping of Endocardial Focal Site of Ventricular Activation, *Pace*, vol. 14, Pt. 1, pp. 557–574, Apr. 1991.

Pollak et al., Intraoperative Identification of a Radiofrequency Lesion Allowing Validation of Catheter Mapping of Ventricular Tachycardia with a Computerized Balloon Mapping System, *Pace*, vol. 15, pp. 854–858, Jun. 1992.

Chen et al., Reappraisal of Electrical Cure of Atrioventricular Nodal Reentrant Tachycardia—Lesions from a Modified Catheter Albation Technique, *International Journal of Cardiology*, vol. 37, pp. 51–60, 1992.

Chen et al., Radiofrequency Catheter Albaltion For Treatment of Wolff–Parkinson–White Syndrome–Short–and Long–Term Follow–up, *International Journal of Cardiology*, vol. 37, pp. 199–207, 1992.

Scheinman, North American Society of Pacing and Electrophysiology (NASPE) Survey on Radiofrequency Catheter Ablation: Implications for Clinicians, Third Party Insurers, and Government Regulatory Agencies, *Pace*, vol. 15, pp. 2228–2231, Dec. 1992.

Silka et al., Phase Image Analysis of Anomalour Ventricular Activation in Petiatric Patients with Pre–excitation Syndromes or Ventricular Tachycardia, *American Heart Journal*, vol. 125, No. 2, Pt. 1, pp. 372–380, Feb. 1993.

Josephson, Clinical Cardiac Electrophysiology: Techniques and Interpretations, 2nd Ed., pp. 566–580, 608–615, 770–783, *Lea & Febiger*, Malvern, Pa., 1993.

Holt et al., Ventricular Arrhythmias—A Guide to Their Localization, *British Heart Journal*, vol. 53, pp. 417–430, 1985.

Joseph et al., Role of Catheter Mapping in the Preoperative Evaluation of Ventricular Tachycardia, *American Journal of Cardiology*, vol. 40, pp. 207–220, Jan. 1982.

Kucher et al., Electrocardiographic Localization of the Site of Ventricular Tachycardia in Patients with Prior Myocardial Infarction, *JACC*, vol. 13, No. 4 pp. 893–900.

Page, Surgical Treatment of Ventricular Tachycardia: Regional Cryoablation Guided by Computerized Epicardial and Endocardial Mapping, *Circulation*, vol. 80, (Supplement I), No. 3, pp. I124 –I–134, Sep. 1989.

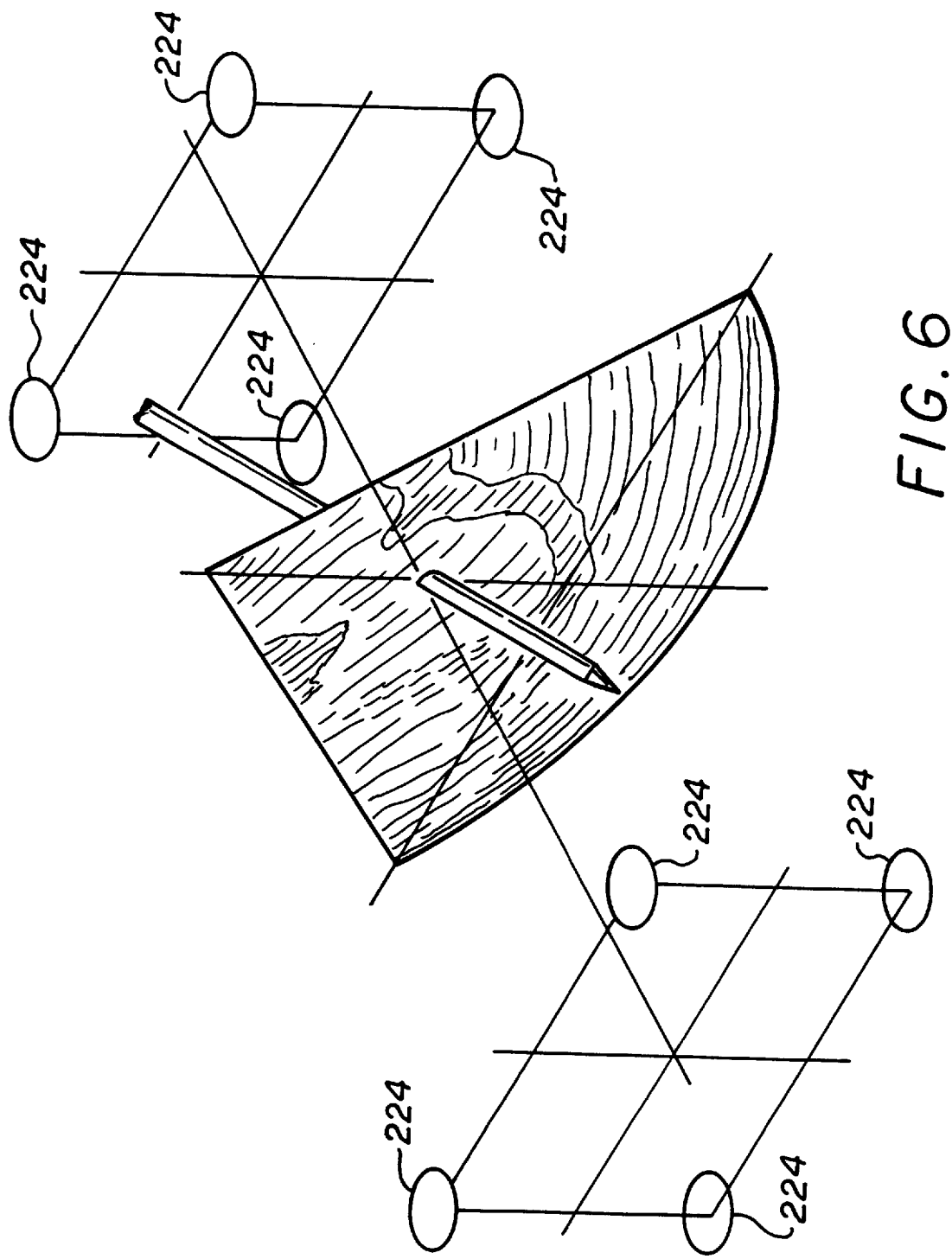

SYSTEM FOR DISPLAYING A 2-D ULTRASOUND IMAGE WITHIN A 3-D VIEWING ENVIRONMENT

RELATED APPLICATIONS

This is a continuation-in-part of International application Ser. No. PCT/CA96/00194, filed on Mar. 24, 1996 and which designated the U.S., which is a CIP of Ser. No. 08/411,959 filed Mar. 28, 1995, now U.S. Pat. No. 5,515,853.

FIELD OF INVENTION

The present invention relates in general to a system for generating images, and more particularly to a system for displaying a 2-dimensional ultrasound image within a 3-dimensional viewing environment.

BACKGROUND OF THE INVENTION

A large number of diagnostic and surgical procedures are performed with the assistance of conventional 2-D echo imaging techniques. In this respect, the physician manipulates a surgical instrument (e.g., a probe or catheter) inside the patient's body, and at the same time tilts the imaging head of the echo machine until the ultrasound beam transects the instrument and the instrument becomes visible on a display monitor. Very often, the instruments are located after considerable "hunting", and the process itself is quite cumbersome. This procedure is often used in the case of amniocentesis and biopsies. In each case, needle or "biting" tools are inserted under ultrasound imaging guidance. In the case of amniocentesis, a physician inserts a needle through the abdomen into the uterus, while at the same time an assistant holds the ultrasound probe steady, making sure that it transects the amniocentesis needle, so that the needle can be visualized.

Conventional 2-D echocardiography provides less-than-adequate information to the physician since the cardiac structures, such as the mitral valve, are very complex and their shape is difficult to interpret from these images. 3-D echocardiography has the potential of solving many of the current visualization problems of cardiac anatomy. As 3-D echo has become developed, however, it has become clear that there are a new set of problems. The first problems deals with the ability to acquire the data in a reasonable time frame. The fundamental issue is time of flight of ultrasound. In this respect, to image the heart, ultrasound must be sent into the tissue to a depth of 15 cm and back again. Given that the speed of sound in cardiac tissue is about 1500 m/sec, that process takes 0.2 msec. To get a good picture, 200 lines are needed. Therefore, 40 msec are required for each image. This results in an imaging rate of 25 Hz. Since this rate is just barely high enough for 2-D, there has been a push in the technology to reach rates of 30 Hz or 50 Hz. To get 3-D ultrasound volumes, about 100 of the 2-D images must be acquired. This means that using conventional technologies, a new volume is acquired every 2 to 3 seconds. This process can generate good 3-D images for most internal organs and other static structures, such as the prostate or a fetus, but does not work for the heart, which is constantly moving.

Other known systems aim to increase the data rate by a factor of 100 so that volumes can be obtained instead of just 2-D images. One such system is described in U.S. Pat. No. 4,949,310 (hereinafter the '310 patent). This system attempts to produce real time 3-D ultrasound images through an exercise in compromise and optimization of many parameters that affect the speed of ultrasound image acquisition. Some of these schemes involve receiving data from several channels at once through dynamic focussing, and reducing the resolution of the images both spatially and temporally.

Once these 3-D image sets are acquired, however, the next issue is how to display the information. In this respect volume thresholding and surface rendering have proven to be extremely difficult in ultrasound images, since they are inherently very noisy. 3-D surfaces cannot be easily extracted, since considerable image processing needs to be done on the data sets. Such post-processing can involve schemes such as (i) dilation of seed points, (ii) skeletonization of larger structures, and (iii) continuity checking and filling to generate some reasonably looking 3-D surfaces. None of this can presently be done in real time, even if the 3-D ultrasound data can be acquired with technology described in the '310 patent.

The system described in the '310 patent uses a multiple plane display. In this respect, the real time volume data sets are intersected by a number of planes, and the intersection of the volume data set with that plane is "mapped" onto that plane. If the plane is placed in a direction orthogonal to the data set axes, then mapping of the data plane onto the visualization plane is relatively straight forward. In this respect, an appropriate 2-D matrix of pixels is extracted from a 3-D set. If the plane is inclined to the original axes, then image extraction and interpolation of pixels needs to be done. There are a number of established algorithms for this process. The system of the '310 patent therefore makes use of multiple viewing planes passed through the 3-D data set, onto which the appropriate 2-D images are "texture mapped" using the appropriate graphical hardware. Such texture mapping hardware can be found on many high end computers, such as those from Silicon Graphics, Inc.

A simpler alternative to the real-time 3-D ultrasound system is one in which images are built up over a large time frame, and then played back in a way to visualize the data set. In the case of the heart, one can acquire high resolution images of the beating heart for many cardiac cycles. If a volume data set is to contain 100 slices of the heart, then one can acquire these slices in 100 heart beats, assuming the 2-D ultrasound system acquires data 30 times per second, and that each heart beat lasts one second. During the first heart beat, the ultrasound imaging transducer is located at one viewing position, such as the apex of the heart, and records 30 images during the heart beat. Therefore one slice of the heart is obtained, imaged 30 times during the heart beat. On the next heart beat, the ultrasound imaging transducer is positioned at an imaging plane slightly away, beside the first imaging plane and another 30 images are obtained during the second heart beat. This process is repeated so that 100 adjacent imaging planes are acquired over 100 cardiac cycles. In each case, each set of 30 images describes the motion of the heart at that particular slice location. In total, the complete heart has been imaged in 100 sections, over 30 time points in the cardiac cycle. These images are then reformatted such that they are expressed not as 100 data sets of 30 images, but rather as 30 sets of 100 images. Each set of images is a snap shot of the 3-D volume of the heart at a particular instant in the cardiac cycle, and there are now 30 copies of this 3-D data set, as it changes through the cardiac cycle. This one cardiac cycle can then be played back on the computer screen in some appropriate format.

As in the system of the '310 patent discussed above, the format that is often chosen is to project a portion of the data set onto a plane that cuts through the data set, and play back the cardiac cycle over and over. U.S. Pat. Nos. 5,454,371 and 5,562,095 describe a means of acquiring and displaying 3-D ultrasound images. The system for displaying the 3-D images operates in the following manner. A cube of data is displayed in perspective on a computer screen, with each of the 6 faces having the corresponding plane of ultrasound image data mapped onto them. These faces can be pushed into the cube interactively by moving a computer mouse. As the face of the cube is moved inward, a new intersection plane of the data set is computed, corresponding to the position of the face, and the appropriate image is mapped onto that plane. During this process, the visible faces of the cube represent the moving ultrasound images, as the whole 3-D data set is played back over and over through the single cardiac cycle reconstructed from the original many cardiac cycles. Like the system of the '310 patent described above, this approach makes use of mapping a particular imaging plane of a previously acquired data set onto a given plane that the user chooses to visualize at that time. The wire frame box that describes the position and orientation of the original 3-D data set and the current plane is very useful in helping to orient the user of the system to the anatomical position of the image that is being displayed. In this respect, FIG. 1A illustrates an orthogonal slice, and FIG. 1B illustrates an oblique slice.

One of the disadvantages of this system is that it can only show a play back of the previously acquired ultrasound data set. It must also be realized that such a visualization scheme provides only one imaging plane at a time. The user selects the imaging plane and watches the playback of the data set. While a user can push the imaging plane back and forth and tilt it sideways to view alternative imaging planes, only one imaging plane is viewed at a time. The utility of this display format is that the user retains information in his mind about where the previous imaging plane was located and how the structures change as the imaging plane is moved and tilted. Ultimately, the 3-D model of the structure is built up in the user's mind, as the user manipulates the 2-D planes and interactively builds up enough information in the user's head. In reality, the complete volume of information is not necessary, only the ability to view an arbitrary plane at a given time (see FIG. 2).

It is known that using the time-of-flight principle of high frequency sound waves, it is possible to accurately measure distances within an aqueous medium, such as inside the body of a living being during a surgical procedure. High frequency sound, or ultrasound, is defined as vibrational energy that ranges in frequency from 100 kHz to 10 MHz. The device used to obtain three-dimensional measurements using sound waves is known as a sonomicrometer. Typically, a sonomicrometer consists of a pair of piezoelectric transducers (i.e., one transducer acts as a transmitter while the other transducer acts as a receiver). The transducers are implanted into a medium, and connected to electronic circuitry. To measure the distance between the transducers, the transmitter is electrically energized to produce ultrasound. The resulting sound wave then propagates through the medium until it is detected by the receiver.

The transmitter typically takes the form of a piezoelectric crystal that is energized by a high voltage spike, or impulse function lasting under a microsecond. This causes the piezoelectric crystal to oscillate at its own characteristic resonant frequency. The envelope of the transmitter signal decays rapidly with time, usually producing a train of six or more cycles that propagate away from the transmitter through the aqueous medium. The sound energy also attenuates with every interface that it encounters.

The receiver also typically takes the form of a piezoelectric crystal (with similar characteristics to the transmitter piezoelectric crystal) that detects the sound energy produced by the transmitter and begins to vibrate in response thereto. This vibration produces an electronic signal in the order of millivolts, that can be amplified by appropriate receiver circuitry.

The propagation velocity of ultrasound in an aqueous medium is well documented. The distance traveled by a pulse of ultrasound can therefore be measured simply by recording the time delay between the instant the sound is transmitted and when it is received. Three-dimensional coordinates can be determined from the distance measurement.

The present invention applies the foregoing principles to overcome the drawbacks of prior art 2-dimensional echo imaging systems to provide a system which allows manipulation of 2-D ultrasound images in 3-D space, within a coordinate system that provides a reference frame. This enables the user to interactively make up a mental construct of the structure under analysis.

SUMMARY OF THE INVENTION

According to the present invention there is provided an echo imaging system for displaying a 2-D ultrasound image in a 3-D viewing environment.

It is an object of the present invention to provide an echo imaging system wherein the user has the ability to visualize the position and progression of surgical instruments.

It is another object of the present invention to provide an echo imaging system that provides image feedback and verification that the intended bodily structure is being operated upon.

It is still another object of the present invention to provide a detachable device for modifying a conventional 2-D ultrasound imaging head to include 3-D tracking capability.

It is yet another object of the present invention to provide a device attachable to a conventional 2-D ultrasound imaging head to provide the 3-D position of the 2-D ultrasound image.

Still other objects and advantages of the invention will become apparent to those skilled in the art upon a reading and understanding of the following detailed description, accompanying drawings and appended claims.

BRIEF DESCRIPTION OF THE DRAWINGS

The invention may take physical form in certain parts and arrangements of parts, a preferred embodiment and method of which will be described in detail in this specification and illustrated in the accompanying drawings which form a part hereof, and wherein:

FIG. 6 is a 3-D scene showing a reference frame, location and direction of a surgical instrument and an ultrasound sector image.

DETAILED DESCRIPTION OF THE PREFERRED EMBODIMENT

Figure 1A:
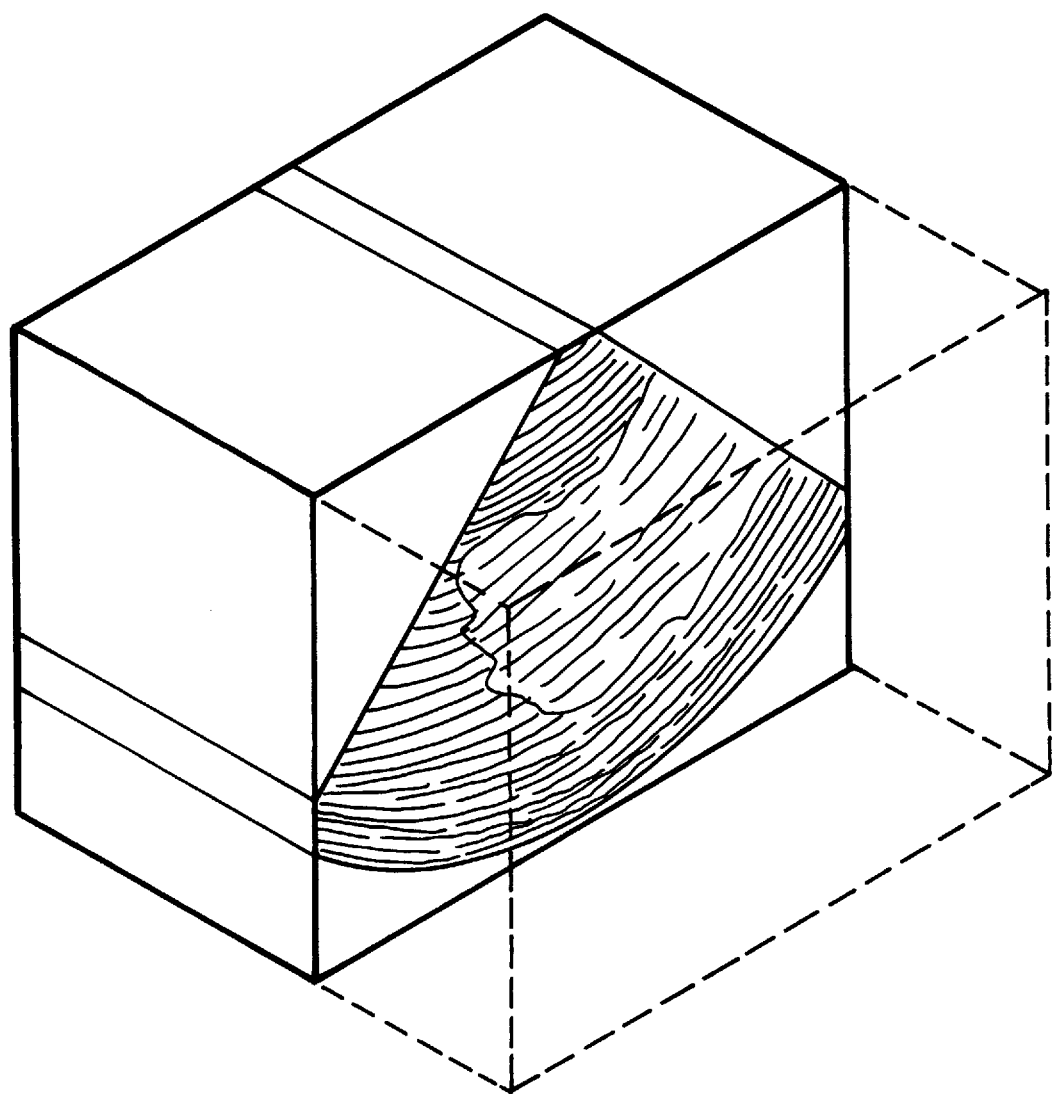
FIGS. 1A and 1B are exemplary displays provided by a conventional 3-D ultrasound system.
Figure 1B:
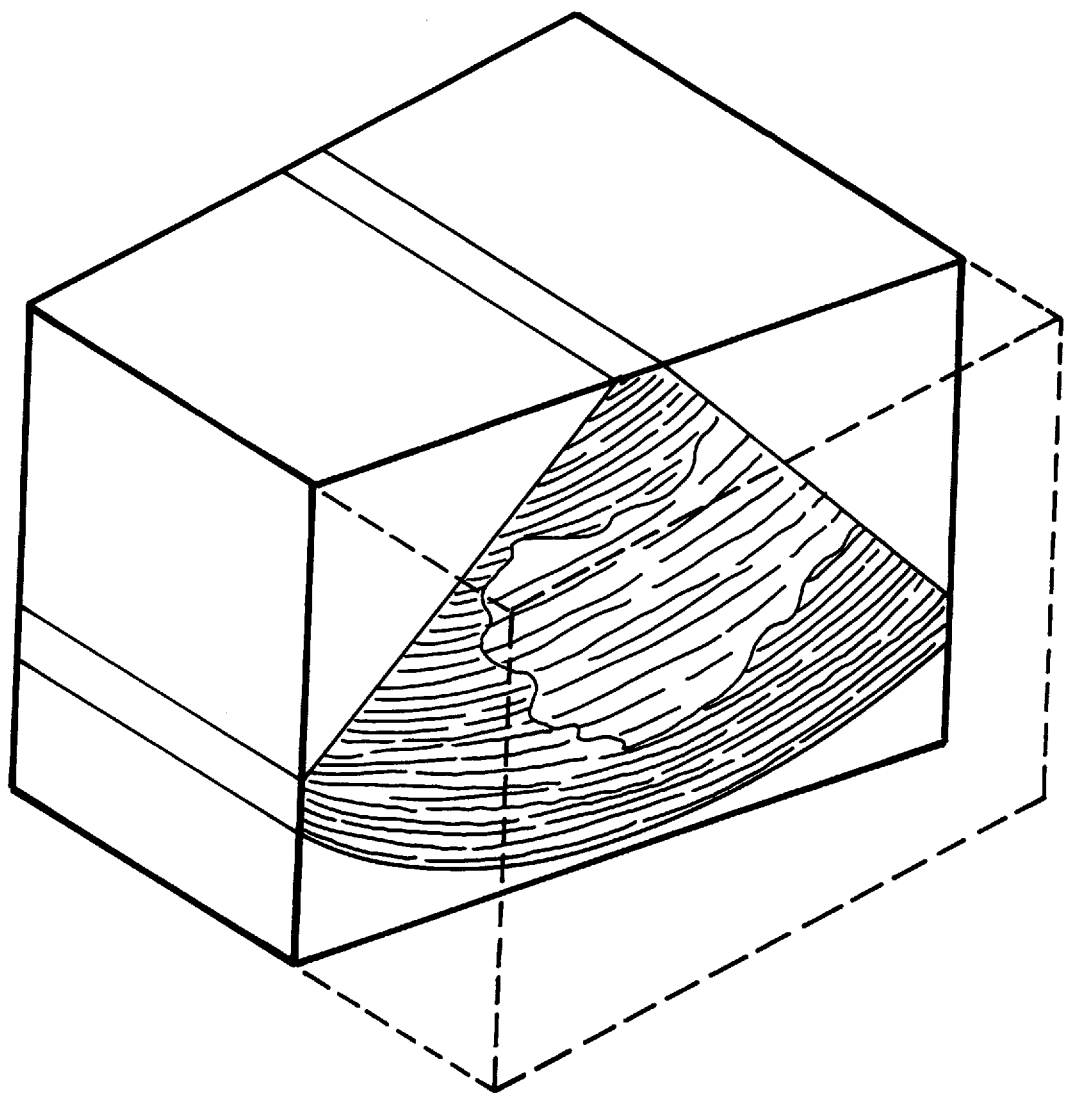
Figure 2:
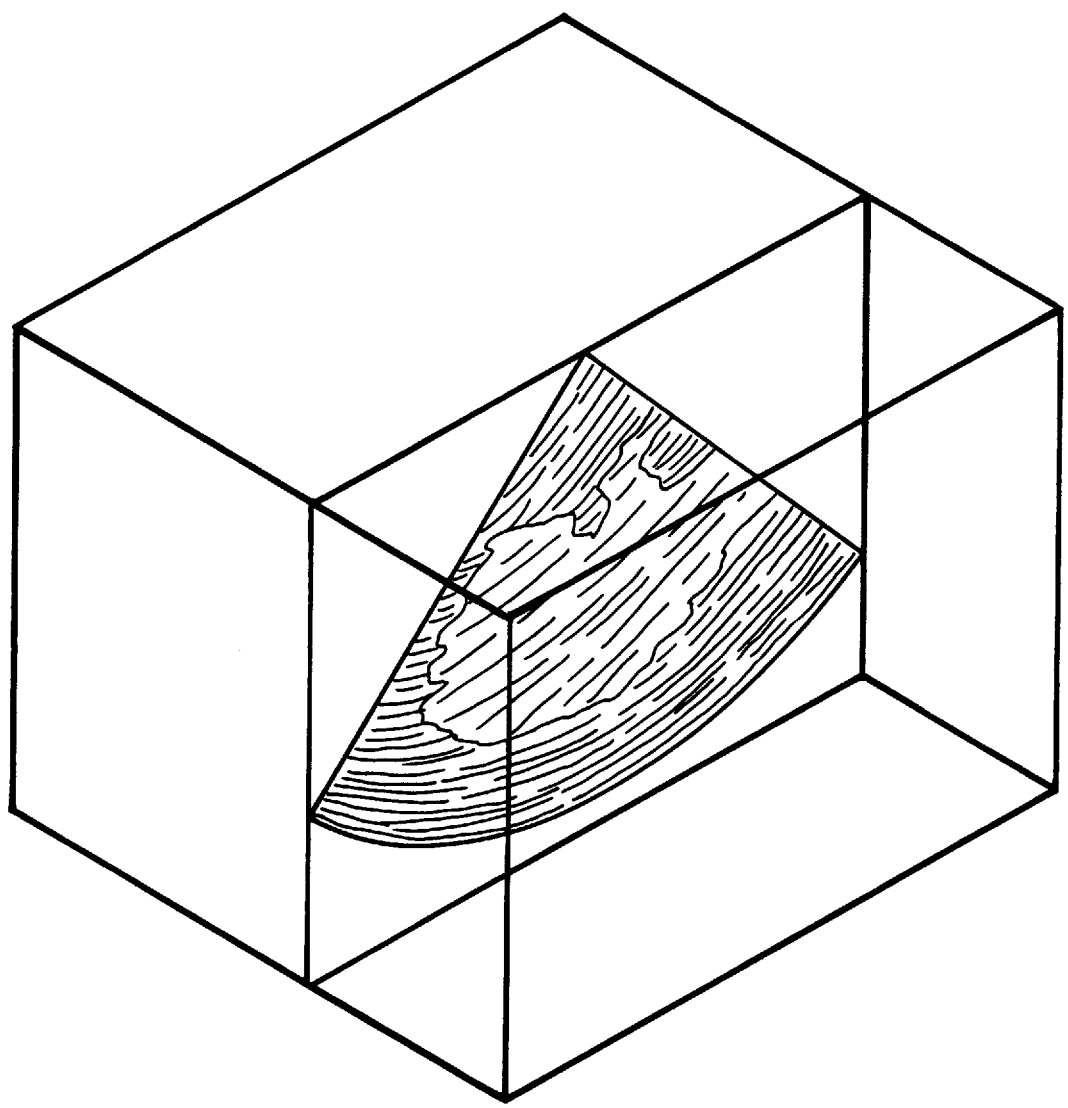
FIG. 2 is an exemplary display of the usable information provided by a conventional 3-D ultrasound system.
Figure 3:
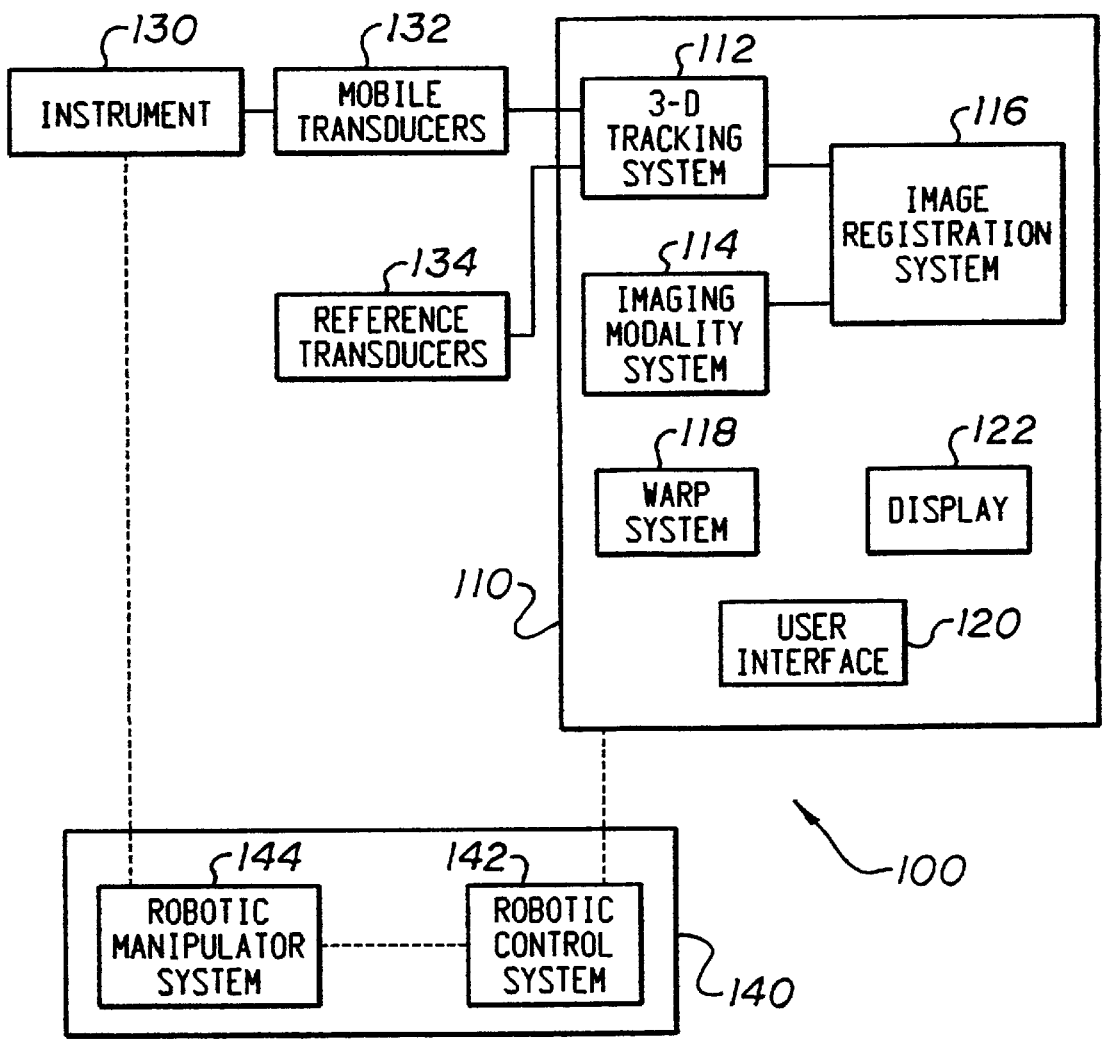
FIG. 3 is a block diagram of a 3-D ultrasound tracking and imaging system, in accordance with a preferred embodiment of the present invention.

Referring now to the drawings wherein the showings are for the purposes of illustrating a preferred embodiment of the invention only and not for purposes of limiting same, FIG. 3 shows a three-dimensional (3-D) tracking and imaging system 100 for use in connection with the echo imaging system of the present invention. 3-D tracking and imaging system 100 is generally comprised of a computer system 110, mobile transducers 132, reference transducers 134, an instrument 130 and an optional robotics subsystem 140.

Computer system 110 is generally comprised of a 3-D tracking system 112, an imaging modality system 114, an image registration system 116, an image warping and geometry transformation system 118 ("warp system"), a user interface 120 and a display 122. It should be appreciated that 3-D tracking system 112 may take the form of a sound-based system or an electromagnetic-based system. Both time of flight and phase relationships may be used to determine distance. Preferably, 3-D tracking system 112 takes the form of the 3-D ultrasound tracking system described in U.S. Pat. No. 5,515,853 and PCT Application No. WO96/31753, both of which are incorporated herein by reference.

Instrument 130 may take the form of a catheter, a probe, a sensor, a needle, a scalpel, a forcep or other device or instrument used in a surgical or diagnostic procedure. Mobile transducers 132 and reference transducers 134 may take the form of an ultrasonic transducer or an electronic transducer. However, for purpose of illustrating a preferred embodiment of the present invention, transducers 132 and 134 will take the form of ultrasonic transducers (i.e., piezoelectric crystals).

A plurality of mobile transducers 132 are fitted to instrument 130. One or more reference transducers 134 provide a reference position relative to mobile transducers 132. In this respect, reference transducers 134 may be located to provide an internal reference frame inside a patient's body or on the surface of a patient body to provide an external reference frame.

As indicated above, reference transducers 134 may be transmitters, transceivers or receivers that can generate ultrasound or electromagnetic radiation, that can be detected by mobile transducers 132.

3-D tracking system 112 transforms the multiple distance measurements between all of the transducers 132, 134 into XYZ coordinates relative to a referenced axis, as described in detail above. It should be appreciated that the reference frame provided by reference transducers 134 must be self-determining that is, if the reference frame becomes distorted, this distortion needs to be detected by reference transducers 134. Detection is typically done by using transceivers that can determine the distance between any combination of two transducers, and hence their relative spacial coordinates in 3-D space. In this regard, the position of the transducers is obtained in 3-D from the images acquired of the bodily structure (e.g., tissue/organ) that show "dots" where the transducers are located, and also from the transducers themselves when they are in the bodily structure. If there is some discrepancy in the distances between all combinations of transducers, then the bodily structure must have deformed (i.e., "warped") after the images were acquired. A mathematical coordinate transformation can be used to specify exactly how to correct the image set and account for the warping. The distance between any combination of two transducers is determined by having each transducer send a signal to all other transducers. In this way, all the distances between the transducers is known. From these distances, XYZ coordinates can be calculated, in reference to some transducer as the origin.

Imaging modality system 114 acquires 2D, 3-D or 4-D image data sets from an imaging source, such as an MRI (magnetic resonance imaging), CT (computerized tomography) or 2-D or 3-D ultrasound device, to provide a "template" through or against which the shape, position and movement of instrument 130 being tracked can be displayed. The template typically takes the form of an image of the environment surrounding the instrument (e.g., a bodily structure). It should be noted that if multiple (3-D) volumes are acquired at different time intervals, a 4-D image is obtained (i.e., 3-D image changing over time).

Image registration system 116 registers the position of instrument 130 within the spatial coordinates of the image data set provided by imaging modality system 114. The position of instrument 130 is provided by the 3-D tracking system 112. Image registration system 116 will provide a display of instrument 130 at its proper 3-D location inside the bodily structure and orientation relative to the bodily structure itself It should be appreciated that registration system 116 may be user assisted, or completely automated if image processing algorithms are implemented to automatically detect the spacial locations of the transducers (typically the reference transducers) in the image data set.

Warp system 118 is a software-based system that transforms or "warps" the image data sets by the appropriate values to correspond to a deformation that has occurred in the reference frame between the time that the image data set were acquired and the time that the procedure is to be implemented during surgery. Accordingly, warp system 118 is typically comprised of a matrix transformation routine that maps the deformed geometry onto the original image data set, and distorts it appropriately.

User interface 120 enables a user to interact with computer system 110, including programming computer system 110 to perform a desired function. For example, a particular view for display can be selected. Instruments 130 (e.g., probes or catheters) can be activated using user interface 120. Display 122 displays to the user registered images provided by image registration system 116.

Optional robotics system 140 is generally comprised of a robotics control system 142 and a robotic manipulator system 144. Robotics control system 142 controls robotic manipulator system 144 to follow a programmed path that can be appropriately changed, based on shifting, warping or changes in the shape of a bodily structure at the time of surgery. Robotic manipulator system 144 physically moves instrument 130 as instructed by robotic control system 142.

The present invention is directed to an echo imaging system which displays a 2-D ultrasound image in a 3-D viewing environment. In this regard, several reference transducers are placed on the back and/or abdomen of the patient and a simple coordinate system is generated on the computer display, showing the direction towards the head and feet, the left and right sides of the patient, and the front and back. Initially, this would appear on the display as an empty box with simple graphics or arrows, as well as the surface transducers shown graphically. A plurality of mobile "position" transducers are mounted to the ultrasound imaging head of an imaging probe. Accordingly, when the imaging probe is placed on the chest or the abdomen, the location and angle of the imaging plane being acquired by the imaging head's imaging transducer can be displayed within a 3-D environment. This 3-D scene can be visualized from any viewpoint by simply moving the mouse and rotating the visual scene on the computer display.

Figure 4:
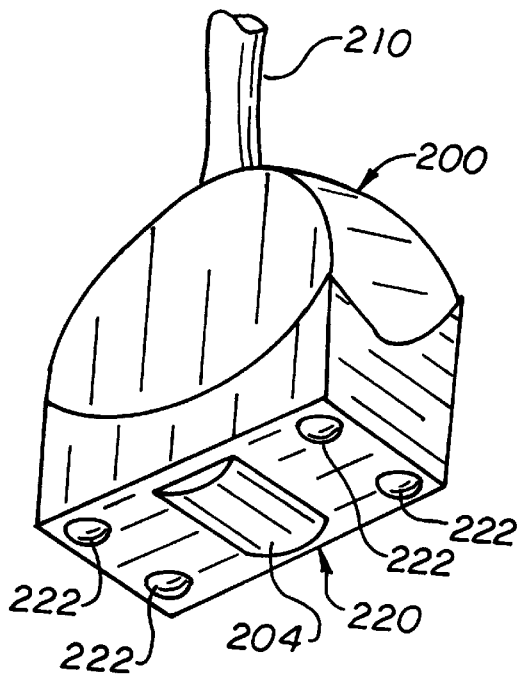
FIG. 4 is a perspective view of an ultrasound imaging head with a detachable tracking clip attached thereto, according to a preferred embodiment of the present invention.
Figure 5:
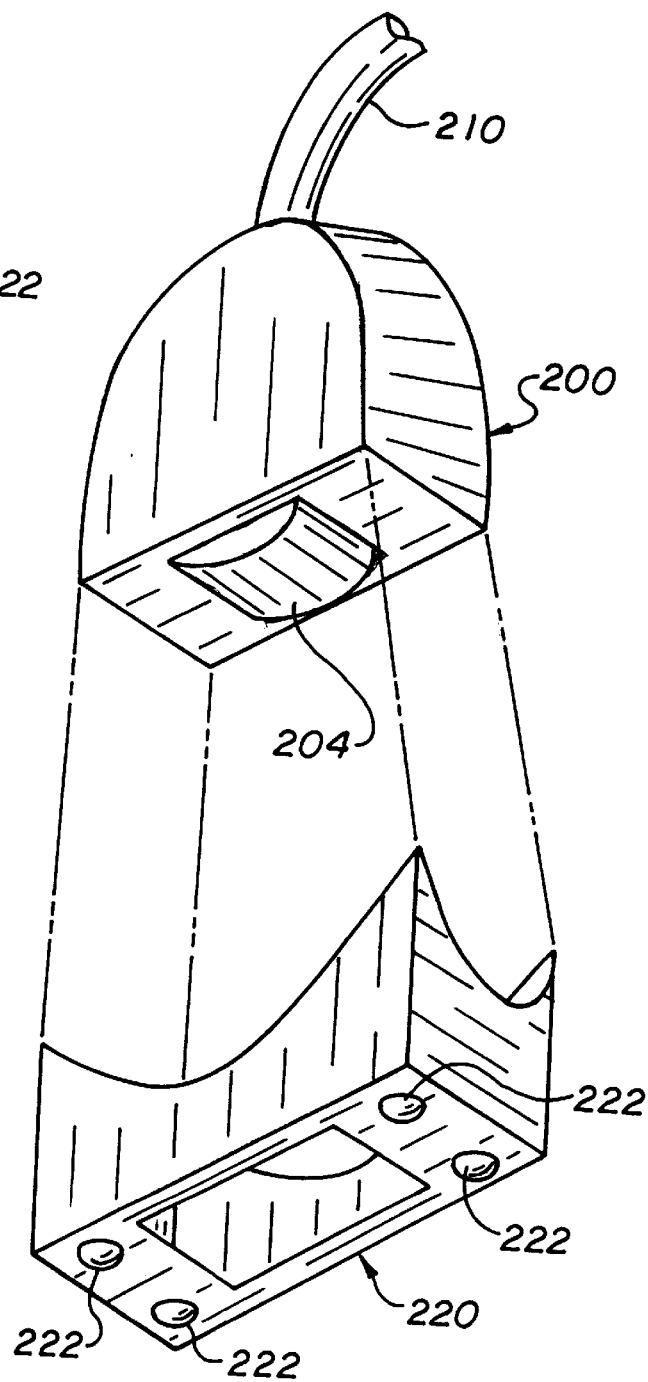
FIG. 5 is an exploded view of the ultrasound imaging head and detachable tracking clip attached thereto, as shown in FIG. 4.

A preferred embodiment of an echo imaging system according to the present invention will now be described in detail with reference to FIGS. 3–5. A typical echo machine ultrasound imaging head 200 has a plastic hand held component with a cable 210 that connects to a main unit (not shown). Imaging head 200 has a window through which ultrasound is transmitted and received by an ultrasound transducer 204. The ultrasound imaging head 200 is fitted with a transducer housing 220 which takes the form of a detachable tracking clip that is attachable to imaging head 200. An exploded view is shown in FIG. 5.

Transducer housing 220 holds three or more position transducers 222 that form a plane perpendicular to the imaging beam. Thus, position transducers 222 reside between imaging head 200 and the skin that imaging head 200 contacts. It should be appreciated that while four position transducers 222 are shown in FIGS. 4 and 5, only three position transducers 222 are need to measure all angles. Reference transducers 224 (see FIG. 6) are mounted to the patient's skin (e.g., back and chest).

As imaging head 200 is tilted and angulated while pressed against the abdomen, the coordinates of position transducers 222 define a plane that is perpendicular to the ultrasound imaging beam. Accordingly, the 3-D coordinates of the imaging plane are determined from the coordinates of position transducers 222. It should be noted that transducer housing 220 makes contact with the abdomen. Alternatively, the imaging head can articulate relative to the transducer plane by means of a gimbal fitted with electronic potentiometers that can relate the angle of the imaging plane relative to the transducer plane that glides flat along the patient's skin. Once the position and orientation of the imaging plane is known in 3-D space relative to the coordinate system of the patient, the typical pie-shaped sector scan produced by ultrasound imaging head 200 can be inserted into the 3-D scene of the patient. Since, the 3-D scene will therefore contain a perspective rendering of the patient frame of reference, the pie-shaped ultrasound sector scan image, is properly oriented within the 3-D scene, as shown in FIG. 6.

The ultrasound image may be shown in real-time in perspective by texture-mapping the video signal onto a pie-shaped polygon drawn in the 3-D scene. The current generation of graphics computers enable this type of real-time image transformation. It should be noted that the location of all of the transducers with respect to each other can be determined in the manner discussed above. One of the transducer locations is chosen as the origin, another as the x axis, and a third as the y axis, and a fourth as the z axis. The coordinates system may be defined by the user. The orientation of imaging plane is calculated from the angle of the four imaging head position transducers 222, and the coordinate system defined by the reference transducers mounted to the patient's body.

By visualizing the location of the imaging plane relative to the inserted surgical instrument, the imaging head 200 can be more quickly manipulated and angled until it transects a surgical instrument (e.g., an amniocentesis needle). In this respect, mobile transducers are mounted to the surgical instrument in order to provide an outline graphic of the instrument and its current position relative to the reference transducers. Moreover, the shadow of the surgical instrument becomes visible in the texture mapped, real time ultrasound image, and the instrument outline graphic can be shown piercing the ultrasound image where its shadow is visible. Accordingly, a physician can immediately determine in which direction to angulate imaging head 200 or move the surgical instrument to get proper orientation within the visual scene (FIG. 6). Accordingly, the present invention allows for safer, faster and more precise surgical procedures.

The invention has been described with reference to a preferred embodiment. Obviously, modifications and alterations will occur to others upon a reading and understanding of this specification. For instance, electromagnetic waves could be substituted for sound waves, as a means for determining position. Accordingly, the ultrasonic transducers are suitably replaced by electromagnetic transducers. It is intended that all such modifications and alterations be included insofar as they come within the scope of the appended claims or the equivalents thereof

Having thus described the invention, it is now claimed:

1. A method for generating a 2-dimensional ultrasound image in a 3-dimensional viewing environment, the method comprising:

mounting a plurality of mobile transducer means to an ultrasound image transducer means adapted for generating a 2-dimensional echo image plane;

mounting a first reference transducer means to a first fixed location;

mounting a second reference transducer means to a second fixed location;

generating three-dimensional coordinates of the mobile transducer means relative to a reference frame established by the first and second reference transducer means;

registering the 2-dimensional echo image plane with the three-dimensional coordinates; and, displaying the 2-dimensional echo image plane at the three-dimensional coordinates, in relation to the reference frame established by the first and second reference transducer means.

2. A method according to claim 1, wherein said first fixed location is a patient's back, and said second fixed location is a patient's abdomen.

3. A method according to claim 1, wherein said method further comprises the steps of:

mounting a plurality of mobile transducers means to a surgical instrument means;

generating 3-dimensional coordinates of the mobile transducer means mounted to the surgical instrument means, relative to the reference frame established by said first and second reference transducer means;

generating an outline image of the surgical instrument means from the 3-dimensional coordinates of the mobile transducer means mounted to the surgical instrument means; and displaying the outline image of the instrument means.

4. A method according to claim 3, wherein the step of displaying the outline image of the instrument means displays the outline image of said surgical instrument means piercing the 2-dimensional echo image plane.

5. A system for generating a 2-dimensional ultrasound image in a 3-dimensional viewing environment comprising:

image transducer means for generating a 2-D echo image plane;

mobile transducer means mounted to the image transducer means;

first reference transducer means located at a first fixed location;

second reference transducer means located at a second fixed location, wherein the first and second reference transducer means establish a reference frame;

coordinate generation means for generating 3-dimensional coordinates of the mobile transducer means relative to the reference frame;

registration means for registering the 2-dimensional echo image plane with the 3-dimensional coordinates; and display means for displaying the 2-dimensional echo image plane at the 3-dimensional coordinates, in relation to the reference frame.

6. A system according to claim 5, wherein said first fixed location is a patient's back, and said second fixed location is a patient's abdomen.

7. A system according to claim 5, wherein said mobile transducer means are arranged on a detachable housing means mounted to said instrument.

8. A system according to claim 5, wherein said mobile transducer means is comprised of at least three transducers to generate the 3-dimensional coordinates of a plane perpendicular to an imaging beam generated by said image transducer means.

9. A system according to claim 8, wherein image transducer means includes:

an imaging head that is articulatable relative to said mobile transducer means; and potentiometer means for relating the angle of the imaging head relative to the 3-dimensional coordinates of the plane generated by the mobile transducer means.

10. A system according to claim 5, wherein said first reference transducer means is comprised of at least four ultrasonic transducers.

11. A system according to claim 5, wherein said second reference transducer means is comprised of at least four ultrasonic transducers.

12. A system according to claim 5, wherein said system further comprises:

a plurality of mobile transducers adapted to be secured to an associated surgical instrument means;

coordinate generation means for generating 3-dimensional coordinates of at least one the plurality of mobile transducer means mounted to the surgical instrument means, relative to the reference frame established by said first and second reference transducer means;

outline generation means for generating an outline image of the surgical instrument means from the 3-dimensional coordinates of the mobile transducer means mounted to the surgical instrument means, and for displaying the outline image of the surgical instrument means on said display means.

13. A system according to claim 12, wherein the outline generation means displays on said display means said outline image piercing said 2-dimensional echo image plane.

* * * * *